United States Patent [19]

Taylor

[11] Patent Number: 4,877,740
[45] Date of Patent: Oct. 31, 1989

[54] PRODUCTION OF CELLS

[75] Inventor: Stephen C. Taylor, Darlington, England

[73] Assignee: Imperial Chemical Industries plc, London, England

[21] Appl. No.: 60,071

[22] Filed: Jun. 9, 1987

[30] Foreign Application Priority Data

Jun. 19, 1986 [GB] United Kingdom ............... 8614925

[51] Int. Cl.$^4$ ................................................ C12R 1/38
[52] U.S. Cl. .............................. 435/253.3; 435/155; 435/189; 435/877
[58] Field of Search ................. 435/253.3, 189, 155, 435/877

[56] References Cited

U.S. PATENT DOCUMENTS 3,326,770  6/1967  Coty ..................................... 435/248

FOREIGN PATENT DOCUMENTS 76606  4/1983  European Pat. Off. .

OTHER PUBLICATIONS

Chemical Abstracts, 80, 117992t, 1974.
Chemical Abstracts, 79, 27793d, 1973.
Chemical Abstracts, 81, 148261d, 1974.
Chemical Abstracts, 73, 1091z, 1970.
Chemical Abstracts, 75, 148792d, 1971.
Chemical Abstracts, 88, 151886m, 1978.
Chemical Abstracts, 70, 9463f, 1969.
Jerina et al, J. Am. Chem. Soc., 92, 1056–1059, 1970.
Jerina et al., Journal of the American Chemical Society, 1976, 98, 5988–5996.
Reineke et al., Tetrahedron, 1978, 34, 1707–1714.
Gibson et al., Biochemistry, 1970, 9(7), 1631–1635.
Gibson et al., Biochemistry, 1968, 7(7), 2653–2662.
Jerina et al., Archives Biochemical Biophysics, 1971, 142, 394–396.
DeFrank et al., Journal of Bacteriology, 1977, 129(3), 1356–1364.
DeFrank et al., Biochemical and Biophysical Research Communications, 1976, 70(4), 1129.
Walker et al., Journal of General Microbiology 1955, 8, 273–276.

Primary Examiner—Robert A. Wax
Attorney, Agent, or Firm—Cushman, Darby & Cushman

[57] ABSTRACT

A method of growing cells of *Pseudomonas putida*, preferably mutants of strains NCIB 11680 or 11767, to induce in them an enzyme capable of converting an aromatic or substituted aromatic compound to a corresponding cyclic dihydroxy compound. Suitable inducers include pyridine and substituted pyridines.

6 Claims, No Drawings

PRODUCTION OF CELLS

This invention relates to the production of bacterial cells useful in biochemical processes for the production of cylic dihydroxy compounds.

Certain cis 1,2-dihydroxycyclohexadienes are useful in the preparation of novel polymers. In our European Patent Specification No. 76606 B we disclose a process for the production of such dihydroxy cyclohexadienes from aromatic compounds using mutant strains of the species *Pseudomonas putida*, in particular mutants of *P. putida* strains NCIB 11767 and NCIB 11680. The enzyme which catalyses the reaction involved in this process is an aromatic dioxygenase which catalyses a reaction between certain aromatic compounds and oxygen for example the reaction below between benzene and oxygen:

When strains such as *P. putida* NCIB 11767 and NCIB 11680, are fed with aromatics, the dihydroxy cyclohexadiene compounds do not accumulate since they are rapidly further oxidised via catechols to products of intermediary metabolism. However in our European Specification No. 76606 we describe how mutants of these microorganisms may be produced which are unable to oxidise the dihydroxy cyclohexadienes and these compounds as a result accumulate when such mutants are exposed to aromatic substrates. Some of these mutants must be grown in the presence of benzene or toluene if the activity of the aromatic dioxygenase enzyme needed to convert aromatics to dihydroxy cyclohexadienes is to be induced. Some of the mutants are are constitutive for the enzyme which causes production of the dihydroxy cyclohexadienes ("constitutive strains"). These constitutive strains do not require prior enzyme induction by benzene or toluene in order to produce dihydroxy cyclohexadienes.

However both types of mutants have disadvantages when used to produce dihydroxy cyclohexadienes. It is not always practicable to use benzene or toluene or other similar enzyme substrates during growth of microorganisms because of the volatility, flammability and poor water solubility of these compounds. In addition dihydroxy cyclohexadiene products arise from these aromatics during the induction period and may be present in concentrations in excess of 10 mM, thus potentially contaminating the different dihydroxy cyclohexadienes that may subsequently be produced by the same culture. Growth in the presence of these inducers may also select for revertant strains which have regained the ability to oxidise and hence grow on the dihydroxy cyclohexadienes. This is particularly likely to happen in continuous culture. Constitutive mutants are not ideal for growth in continuous culture since in such culture there is a tendency for the constitutive phenotype to be lost.

According to the present invention we provide a method for the production of cells of *Pseudomonas putida* having an enzyme capable of converting an aromatic or substituted aromatic compound to a corresponding cyclic dihydroxy compound containing a 1,2-dihydroxy-cyclohexa-3,5-diene ring which comprises growing cells of a mutant strain of *Pseudomonas putida* (as hereinafter defined) in a culture medium containing an inducer compound (other than benzene or toluene) which causes induction of the enzyme capable of converting the aromatic or substituted aromatic compound to the corresponding cyclic dihydroxy compound and which is not itself a substrate for said enzyme.

The cells produced in the method of the invention may be used as microbial catalysts for the production of cyclic dihydroxy compounds from aromatics by the process of our European Pat. No. 76606 B or by alternative processes described in the literature (e.g. Gibson D. T. et al, Biochemistry, 9, 1970, 1626–1630).

Microbial cells produced by the method of the invention may be used to convert a wide range of aromatic and substituted aromatic compounds into corresponding cyclic dihydroxy compounds. Preferably the aromatic or substituted aromatic compound is monocyclic but it may also comprise a plurality of rings, e.g. naphthalene and biphenyl. The substituted aromatic compound may have one or more substituents. Possible substituents include alkyl groups, e.g. methyl or ethyl, vinyl groups, organic groups containing e.g. nitrogen, sulphur or halogen atoms and halide groups. Particular aromatic and substituted aromatic compounds which may be converted by cells produced by the method of the invention include benzene (converted to cis-1,2-dihydroxy cyclohexa-3,5-diene), chlorobenzene, toluene, fluorobenzene, benzyl alcohol and naphthalene.

The cells produced by the method of the present invention may be used in conversions to produce compounds having the general formula:

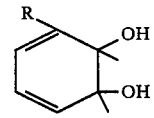

wherein R is a —C trihalide, —O alkyl or —O phenyl group, which are claimed in our divisional application, particularly the compound where R is —CF$_3$.

The mutant strain used in the method of the present invention is a strain of *Pseudomonas putida*:
(a) in which an enzyme can be induced which can convert an aromatic or substituted aromatic compound into a corresponding cyclic dihydroxy compound,
(b) which is not capable of growing on benzene or toluene, and
(c) which is derived from a strain of *P. putida* which is capable of growth on benzene or toluene.

Preferably the mutant strain is derived from *P. putida* strain NCIB 11680 or NCIB 11767 deposited at the National Collection of Industrial Bacteria, Torrey Research Station, Aberdeen, Scotland, UK.

Compounds suitable as the inducer compound in the method of the invention include cyclohexane, cyclohexanol, cis 1,2-dihydroxycyclohexa-3,5-diene, furan, thiophene, benzofuran, cyclohexadiene, coumarin and 1,3,5-trimethylbenzene. However the most effective inducer compounds and thus those which are preferably used are pyridine and some related compounds, in particular pyridine and substituted pyridines, especially suitable compounds are pyridene and methyl substituted pyridines, e.g. α-picoline and β-picoline. Preferred inducer compounds are miscible with water and have limited volatility and flammability. Preferably the inducer compound is included in the culture medium in a concentration in the range 0.01 mM to 2 mM.

Strains which are very suitable as mutant strains in the method of the invention, may be prepared by treating *Pseudomonas putida* NCIB 11680 or preferably *Pseudomonas putida* NCIB 11767 under mutating conditions therefor to give mutant strains which are no longer capable of utilising toluene or benzene as a sole source of carbon for growth as described in our European Pat. No. 76606B.

In the method of the invention, cells of the mutant strain may be grown in a conventional growth medium (modified to include an inducer compound) as a continuous, batch or fed-batch technique. The method is most valuable for growing cells in continuous culture.

The growth medium used may comprise any suitable carbon source and an aqueous mineral salts solution. The carbon source may be, for example, acetic acid, glucose or ethanol. The concentration of carbon source can vary over a wide range but is generally between 1% (w/w) and 20% (w/w). Oxygen, or an oxygen containing gas, must be present during the growth period. The temperature of the medium during the growth period may vary considerably but normally will be in the range of 25° C. to 35° C. The pH of the medium is kept in the range of 5.5 to 8.0 during growth and preferably at 6.5 to 7.5. The size of the culture can vary considerably for example between 1.5 and 500 liters.

Following the growth period the cells can be used to carry out conversions as described in our European Pat. No. 76606B.

Some of the other cyclic dihydroxy compounds which can be produced using microbial cells produced in the method of the invention can be used to produce phenols and catechols which are useful as intermediates in the production of drugs, herbicides and insecticides or as chiral synthons from which for example certain natural products may be synthesised.

Growth media used in preparation of mutants and in Examples

1. Bauschop and Elsdon's medium as described in Journal of General Microbiology, 1960, Volume 23, pages 457–469.

2. Luria liquid medium as described in "Experiments in Molecular Genetics" by J H Miller, published by Cold Spring Harbor Laboratories, New York, 1972.

Preparation of mutant strains of *Pseudomonas putida* NCIB 11767 for use in the present invention

*Pseudomonas putida* NCIB 11767 was grown to early exponential phase in Luria liquid medium. The cells were harvested by centrifugation and resuspended at a concentration of 0.2 grams dry cell weight per liter in 20 ml of 25 millimolar citric acid-sodium citrate buffer, pH 5.5 containing 1 mg of N-methyl-N'-nitro-N-nitroso-guanidine (NTG). After 45 minutes at 30° C. the cells were harvested by centrifugation, washed twice with Bauschop and Elsdon's medium and then grown overnight in this medium when containing 0.3% (w/v) sodium pyruvate at 30° C. After serial dilution, cells were plated on a Bauschop and Elsdon's medium agar containing 0.3 millimolar sodium pyruvate and incubated in 1 liter paint tins each containing 0.5 ml benzene in a vial. After 3 days at 30° C. 144 prospective mutants, i.e. colonies less than 0.5 mm diameter, were picked off and regrown on a 0.2% w/v sodium pyruvate, Bauschop and Elsdon's medium agar.

90 of these mutants were screened in liquid culture for the production from benzene of a compound absorbing at 260 nm. One mutant which gave a supernatant liquid with a maximum absorbance at 260 nanometers of 37 is hereinafter referred to for convenience as mutant strain B.

The invention is illustrated by the following Examples:

EXAMPLE 1

This example illustrates the induction of aromatic oxidation in Mutant B by the method of the invention using a range of compounds which are not substrates for the enzyme in question which converts benzene and toluene to benzene cis-glycol(cis 1,2-dihydroxy cyclohexa-3,5-diene and toluene cis-glycol (cis 1,2-dihydroxy-3-methyl cyclohexa-3,5-diene) respectively.

Mutant B was grown overnight at 30° C. in 50 ml of Bauschop and Elsdon's medium containing 0.3% w/v sodium pyruvate and one of a range of possible inducer compounds at a final concentration of 1 mM. After growth each culture was harvested by centrifugation and resuspended in 10 ml of phosphate buffer, pH 7.8 containing 0.4% w/v ethanol to a concentration of 0.5 g dry weight $l^{-1}$. In the centre well of each flask 0.5 ml of toluene was placed and flasks were incubated with shaking at 30° C. After 18 hours the amount of toluene cis-glycol produced in each flask was measured—(Table 1). Several of the potential inducers clearly allowed for significantly greater amounts of toluene cis-glycol to be produced than that seen in cells grown in the absence of any inducer on pyruvate alone or with toluene as inducer. In particular, cyclohexene, cyclohexadiene, pyridine, furan, 1,3,5-trimethylbenzene all gave significantly more toluene cis-glycol production than pyruvate alone or with 1 ml toluene present. The optimum effect when using pyridine was seen at a concentration of <1.0 mM.

TABLE 1

| Inducer compound (conc. 1 mM) | g. Toluene cis-glycol produced per gram cells in 18 h period |
| --- | --- |
| control | 2.7 |
| cyclohexene | 11.7 |
| cyclohexenol | 3.0 |
| benzene-cis-glycol | 3.0 |
| furan | 4.8 |
| thiophene | 4.2 |
| benzofuran | 3.0 |
| cyclohexadiene | 5.4 |
| coumarin | 4.5 |
| 1,3,5 trimethylbenzene | 6.0 |
| toluene | 3.3 |
| pyridine (0.5 mM) | 6.6 |
| pyridine (1.0 mM) | 6.0 |
| pyridine (2.0 mM) | 5.1 |
| α-picoline | 6.4 |
| β-picoline | 7.5 |
| γ-picoline | 1.2 |

EXAMPLE 2

This example illustrates the use of pyridine as an inducer in continuous culture. Mutant B was grown as a 500 ml chemostat culture, at pH 7.0, temperature 30° C., and stirrer rate 500 rpm in Bauschop and Elsdon's medium plus 0.3% w/v sodium pyruvate and 0.5 mM pyridine. A dilution rate of 0.1 $h^{-1}$ was used. At time intervals, samples were removed from the chemostat and assayed for the production of toluene-cis-glycol from toluene as in Example 1. For a period of at least 360 hours, cells retained the ability to produce toluene cis-glycol and there was no reversion of the population to the wild type phenotype as would occur if toluene was used as inducer. The results are set out in Table 2.

TABLE 2

| Duration of culture (h) | No. of wild type cells in population (frequency) | Activity: g.l$^{-1}$ toluene cis-glycol made per gram cells in 18 h period |
| --- | --- | --- |
| 0 | 1.5 × 10$^{-7}$ | 1.8 |
| 7 | | 2.4 |
| 24 | | 17.7 |
| 79 | | 21.0 |
| 149.5 | | 7.4 |
| 246 | 2.5 × 10$^{-8}$ | 14.2 |
| 298 | | 18.1 |
| 360 | 6.8 × 10$^{-9}$ | 13.7 |

I claim:

1. A method for the production of cells of *Pseudomonas putida* having an enzyme capable of converting an aromatic or substituted aromatic compound to a corresponding cyclic dihydroxy compound containing a 1,2-dihydroxy-cyclohexa-3,5-diene ring which comprises growing cells of a mutant strain of *Pseudomonas putida* selected from the group consisting of NCIB 11680, NCIB 11767, strains derived from NCIB 11680 and strains derived from NCIB 11767 in a culture medium containing an inducer compound selected from the group consisting of cyclohexane, cyclohexanol, benzene-cis-glycol, furan, thiophene, benzofuran, cyclohexadiene, coumarin, 1,3,5-trimethylbenzene, pyridine and substituted pyridine which causes induction of the enzyme capable of converting the aromatic or substituted aromatic compound to the corresponding cyclic dihydroxy compound and which is not itself a substrate for said enzyme.

2. A method according to claim 1 wherein the inducer compound is miscible with water.

3. A method according to claim 1 wherein the inducer compound is selected from the group consisting of pyridine, α-picoline and β-picoline.

4. A method according to claim 1 wherein the inducer compound is included in the culture medium in a concentration in the range 0.01 mM to 2 mM.

5. A method according to claim 1 wherein the culture medium contains a carbon source in a concentration in the range 1% to 20% (w/w).

6. A method according to claim 1 which is carried out at a temperature in the range 25° C. to 35° C. and at a pH in the range 5.5 to 8.

* * * * *